United States Patent
Roy et al.

(10) Patent No.: US 10,806,508 B2
(45) Date of Patent: Oct. 20, 2020

(54) METHOD FOR MANUFACTURING AN ELECTRODE ASSEMBLY CONFIGURED FOR USE WITH AN ELECTROSURGICAL INSTRUMENT

(71) Applicant: COVIDIEN LP, Mansfield, MA (US)

(72) Inventors: Jeffrey M. Roy, Boulder, CO (US); Kim V. Brandt, Loveland, CO (US)

(73) Assignee: Covidien LP, Mansfield, MA (US)

( * ) Notice: Subject to any disclaimer, the term of this patent is extended or adjusted under 35 U.S.C. 154(b) by 371 days.

(21) Appl. No.: 15/658,978

(22) Filed: Jul. 25, 2017

(65) Prior Publication Data

US 2017/0319266 A1 Nov. 9, 2017

Related U.S. Application Data

(62) Division of application No. 14/103,971, filed on Dec. 12, 2013, now Pat. No. 9,713,491.

(60) Provisional application No. 61/766,563, filed on Feb. 19, 2013.

(51) Int. Cl.
  *A61B 18/14* (2006.01)
  *A61B 18/00* (2006.01)
  *A61B 17/00* (2006.01)
  *A61B 90/00* (2016.01)

(52) U.S. Cl.
  CPC ............ *A61B 18/1445* (2013.01); *A61B 2017/00526* (2013.01); *A61B 2018/00571* (2013.01); *A61B 2090/034* (2016.02); *Y10T 29/49204* (2015.01)

(58) Field of Classification Search
  CPC .......... A61B 18/1445; A61B 2090/034; A61B 2017/00526; A61B 2018/00571; Y10T 29/49204
  See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |

(Continued)

FOREIGN PATENT DOCUMENTS

| | | |
|---|---|---|
| CN | 201299462 Y | 9/2009 |
| DE | 2415263 A1 | 10/1975 |

(Continued)

OTHER PUBLICATIONS

U.S. Appl. No. 08/926,869, filed Sep. 10, 1997, James G. Chandler.

(Continued)

*Primary Examiner* — Peter Dungba Vo
*Assistant Examiner* — Jeffrey T Carley
(74) *Attorney, Agent, or Firm* — Carter, DeLuca & Farrell LLP

(57) ABSTRACT

A method for manufacturing an electrode configuration configured for use with an electrosurgical instrument is provided. A pre-assembled jaw configuration including jaw members including respective first and second electrodes is provided. One or more stop members are positioned on the first electrode. The first and second electrodes are approximated toward one another for contact therebetween so as to form an at least one indentation on the second electrode.

9 Claims, 3 Drawing Sheets

(56) References Cited

U.S. PATENT DOCUMENTS

| | | |
|---|---|---|
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H001745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H001904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H002037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| 7,150,097 B2 | 12/2006 | Sremcich et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 8,266,783 B2 | 9/2012 | Brandt et al. |
| 8,679,140 B2 | 3/2014 | Butcher |
| RE44,834 E | 4/2014 | Dumbauld et al. |
| 9,713,491 B2 | 7/2017 | Roy et al. |
| 2002/0062123 A1* | 5/2002 | McClurken ............ A61B 18/14 606/34 |
| 2005/0033278 A1* | 2/2005 | McClurken ............ A61B 18/14 606/41 |
| 2005/0131390 A1 | 6/2005 | Heinrich et al. |
| 2011/0060334 A1* | 3/2011 | Brandt ............... A61B 18/1445 606/48 |
| 2011/0072638 A1* | 3/2011 | Brandt ............... A61B 18/1442 29/527.1 |
| 2011/0073246 A1* | 3/2011 | Brandt ............... A61B 18/1445 156/242 |
| 2012/0083783 A1* | 4/2012 | Davison ............ A61B 18/1445 606/45 |
| 2012/0083784 A1* | 4/2012 | Davison ............ A61B 18/1445 606/48 |
| 2013/0014375 A1 | 1/2013 | Hempstead et al. |
| 2013/0071282 A1* | 3/2013 | Fry .................. A61B 18/1445 419/8 |
| 2013/0185922 A1 | 7/2013 | Twomey et al. |
| 2013/0232753 A1* | 9/2013 | Ackley ................ B29C 31/008 29/407.05 |
| 2013/0255063 A1 | 10/2013 | Hart et al. |
| 2013/0292238 A1* | 11/2013 | Petty ..................... H01H 1/12 200/505 |
| 2014/0031821 A1 | 1/2014 | Garrison |
| 2014/0031860 A1 | 1/2014 | Stoddard et al. |
| 2014/0046323 A1 | 2/2014 | Payne et al. |
| 2014/0052128 A1 | 2/2014 | Townsend et al. |
| 2014/0066910 A1 | 3/2014 | Nau, Jr. |
| 2014/0066911 A1 | 3/2014 | Nau, Jr. |
| 2014/0074091 A1 | 3/2014 | Arya et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 102004026179 A1 | 12/2005 |
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 102008018406 B3 | 7/2009 |
| EP | 1281878 A1 | 2/2003 |
| EP | 1159926 A3 | 3/2003 |
| JP | 61501068 | 9/1984 |
| JP | 6502328 | 3/1992 |
| JP | 55106 | 1/1993 |
| JP | H054-0112 A | 2/1993 |
| JP | 6121797 | 5/1994 |
| JP | 6285078 | 10/1994 |
| JP | 6511401 | 12/1994 |
| JP | H63-43644 A | 12/1994 |
| JP | H72-65328 A | 10/1995 |
| JP | H085-6955 A | 3/1996 |
| JP | H82-52263 A | 10/1996 |
| JP | 8289895 | 11/1996 |
| JP | 8317934 | 12/1996 |
| JP | 8317936 | 12/1996 |
| JP | 910223 | 1/1997 |
| JP | H090-00538 A | 1/1997 |
| JP | 9122138 | 5/1997 |
| JP | H10-000195 A | 1/1998 |
| JP | H10-24051 A | 1/1998 |
| JP | 10155798 | 6/1998 |
| JP | 1147149 | 2/1999 |
| JP | 1147150 | 2/1999 |
| JP | 11070124 | 3/1999 |
| JP | 11169381 | 6/1999 |
| JP | 11192238 | 7/1999 |
| JP | 11244298 A | 9/1999 |
| JP | 2000102545 A | 4/2000 |
| JP | 2000135222 A | 5/2000 |

(56) References Cited

FOREIGN PATENT DOCUMENTS

| JP | 2000342599 A | 12/2000 |
|---|---|---|
| JP | 2000350732 A | 12/2000 |
| JP | 20013400 A | 1/2001 |
| JP | 20018944 | 1/2001 |
| JP | 200129355 | 2/2001 |
| JP | 200129356 | 2/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2011125195 A | 6/2011 |
| JP | 6030945 B2 | 11/2016 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2006021269 A1 | 3/2006 |
| WO | 05110264 A3 | 4/2006 |
| WO | 2008040483 A1 | 4/2008 |
| WO | 2011018154 A1 | 2/2011 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 13/731,674, filed Dec. 31, 2012, Siebrecht.
U.S. Appl. No. 14/019,031, filed Sep. 5, 2013, Garrison.
U.S. Appl. No. 14/019,094, filed Sep. 5, 2013, Garrison.
U.S. Appl. No. 14/032,486, filed Sep. 20, 2013, Kendrick.
U.S. Appl. No. 14/035,423, filed Sep. 24, 2013, Garrison.
U.S. Appl. No. 14/037,772, filed Sep. 26, 2013, Frushour.
U.S. Appl. No. 14/041,995, filed Sep. 30, 2013, Kendrick.
U.S. Appl. No. 14/042,947, filed Oct. 1, 2013, Craig.
U.S. Appl. No. 14/043,039, filed Oct. 1, 2013, Rusin.
U.S. Appl. No. 14/043,322, filed Oct. 1, 2013, O'Neill.
U.S. Appl. No. 14/047,474, filed Oct. 7, 2013, Mueller.
U.S. Appl. No. 14/050,593, filed Oct. 10, 2013, Pleven.
U.S. Appl. No. 14/052,827, filed Oct. 14, 2013, Nau.
U.S. Appl. No. 14/052,856, filed Oct. 14, 2013, Latimer.
U.S. Appl. No. 14/052,871, filed Oct. 14, 2013, Kappus.
U.S. Appl. No. 14/054,173, filed Oct. 15, 2013, Payne.
U.S. Appl. No. 14/054,573, filed Oct. 15, 2013, Harper.
U.S. Appl. No. 14/064,310, filed Oct. 28, 2013, Reschke.
U.S. Appl. No. 14/065,644, filed Oct. 29, 2013, Reschke.
U.S. Appl. No. 14/080,564, filed Nov. 14, 2013, Lawes.
U.S. Appl. No. 14/080,581, filed Nov. 14, 2013, Kerr.
U.S. Appl. No. 14/083,696, filed Nov. 19, 2013, Horner.
U.S. Appl. No. 14/086,399, filed Nov. 21, 2013, Allen.
U.S. Appl. No. 14/091,505, filed Nov. 27, 2013, Garrison.
U.S. Appl. No. 14/091,521, filed Nov. 27, 2013, Garrison.
U.S. Appl. No. 14/091,532, filed Nov. 27, 2013, Garrison.
U.S. Appl. No. 14/098,953, filed Dec. 6, 2013, Cunningham.
U.S. Appl. No. 14/100,237, filed Dec. 9, 2013, Reschke.
U.S. Appl. No. 14/103,971, filed Dec. 12, 2013, Roy.
U.S. Appl. No. 14/105,374, filed Dec. 13, 2013, Moua.
U.S. Appl. No. 14/109,459, filed Dec. 17, 2013, Hoarau.
U.S. Appl. No. 14/149,343, filed Jan. 7, 2014, Schmaltz.
U.S. Appl. No. 14/152,618, filed Jan. 10, 2014, Artale.
U.S. Appl. No. 14/152,690, filed Jan. 10, 2014, Hart.
U.S. Appl. No. 14/153,346, filed Jan. 13, 2014, Collings.
U.S. Appl. No. 14/162,192, filed Jan. 23, 2014, Garrison.
U.S. Appl. No. 14/164,569, filed Jan. 27, 2014, Heard.
U.S. Appl. No. 14/169,358, filed Jan. 31, 2014, Reschke.
U.S. Appl. No. 14/172,050, filed Feb. 4, 2014, Johnson.
U.S. Appl. No. 14/173,391, filed Feb. 5, 2014, Kharin.
U.S. Appl. No. 14/176,341, filed Feb. 10, 2014, Hart.
U.S. Appl. No. 14/176,684, filed Feb. 10, 2014, Chojin.
U.S. Appl. No. 14/177,812, filed Feb. 11, 2014, Dycus.
U.S. Appl. No. 14/178,540, filed Feb. 12, 2014, Anderson.
U.S. Appl. No. 14/182,894, filed Feb. 18, 2014, Hart.
U.S. Appl. No. 14/182,967, filed Feb. 18, 2014, Latimer.
U.S. Appl. No. 14/183,090, filed Feb. 18, 2014, Arts.
U.S. Appl. No. 14/188,935, filed Feb. 25, 2014, Reschke.
U.S. Appl. No. 14/196,066, filed Mar. 4, 2014, McCullough.
U.S. Appl. No. 14/204,770, filed Mar. 11, 2014, Dumbauld.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales—Product Literature; Dec. 31, 2000.
Johnson et al. "Evaluation of a Bipolar Electrothermal Vessel Sealing Device in Hemorrhoidectomy" Sales—Product Literature; Jan. 2004.
E. David Crawford "Evaluation of a New Vessel Sealing Device in Urologic Cancer Surgery" Sales—Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales—Product Literature 1999.
LigaSure Vessel Sealing System, the Seal of Confidence in General, Gynecologic, Urologic, and Laparoscopic Surgery; Sales—Product Literature; Apr. 2002.

(56) References Cited

OTHER PUBLICATIONS

Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales—Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales—Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul.-Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales—Product Literature 2000.
Jarrett et al., "Use of the LigaSure Vessel Sealing System for Peri-Hilar Vessels in Laparoscopic Nephrectomy" Sales—Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales—Product Literature 1999.

\* cited by examiner

METHOD FOR MANUFACTURING AN ELECTRODE ASSEMBLY CONFIGURED FOR USE WITH AN ELECTROSURGICAL INSTRUMENT

CROSS REFERENCE TO RELATED APPLICATIONS

The present application is a divisional application of U.S. patent application Ser. No. 14/103,971, filed on Dec. 12, 2013, which claims the benefit of and priority to U.S. Provisional Application Ser. No. 61/766,563, filed on Feb. 19, 2013, the entire contents of which are incorporated herein by reference.

BACKGROUND

Technical Field

The present disclosure relates to a method for manufacturing an electrode assembly configured for use with an electrosurgical instrument. More particularly, the present disclosure relates to a method for manufacturing an electrode assembly including a self-setting electrode configuration.

Description of Related Art

Electrosurgical instruments configured to electrosurgically treat tissue are well known in the art. Typically, the electrosurgical instrument includes a housing, shaft, and an end effector including a pair of jaw members. One or more suitable electrosurgical energy sources may be utilized to provide electrosurgical energy to the jaw members of the end effector. Depending on the electrical configuration of the jaw members, one or both of the jaw members will include an electrode configuration that is configured to supply current thereto for electrosurgically treating, e.g., coagulate, seal, fulgurate, desiccate, etc., tissue.

In certain instances, such as, for example, during a tissue sealing procedure, a precise, well maintained gap between opposing electrodes is required to ensure proper vessel sealing and grasping functions. This gap, which is commonly referred to in the art as "jaw gap," is a function of the individual components as well as the final device assembly process. Variation in these areas may lead to overall variation in "jaw gap" that may result in degradation of performance.

SUMMARY

As can be appreciated, a method for manufacturing an electrode assembly including a self-setting electrode configuration may prove useful in the surgical arena.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the present disclosure provides a method for manufacturing an electrode configuration for an electrosurgical instrument. A jaw configuration including first and second jaw members including respective first and second electrodes thereon is provided. One or more stop members are positioned on the first electrode. The first and second jaw members including the electrodes are approximated toward one another for contact therebetween. And, one or more indentations are formed on the second electrode. The indentation(s) may be configured to provide a jaw gap that ranges from about 0.01 inches to about 0.06 inches. Moreover, during in-situ use of the pre-assembled jaw members, engagement between the at least one stop member and the at least one indentation is configured to prevent jaw splay.

Approximating the first and second jaw members including the electrodes may include compressing the first and second jaw members with a force that is at least twice as much as a force that is utilized to electrosurgically treat tissue in situ. Positioning the stop member(s) may include providing a stop member that is a ceramic dot.

A shim may be provided between the first and second opposing electrodes prior to approximating the first and second jaw members including the electrodes toward one another so as to control a depth of the at least one indentation. A portion of a bottom surface of the second electrode may be removed to facilitate forming the at least one indentation. The portion of the bottom surface may be located directly beneath the position of where the at least one indentation is to be formed. An etching process may be utilized to remove the portion of a bottom surface of the second electrode. Alternatively, a portion of a bottom surface of the second electrode may be chemically treated to facilitate forming the at least one indentation; the portion of the bottom surface is located directly beneath chemically.

An aspect of the present disclosure provides a method for manufacturing an electrode configuration for an electrosurgical instrument. A pre-assembled jaw configuration including first and second jaw members including respective first and second electrodes is provided. One or more stop members are positioned on the first electrode. A portion of a bottom surface of the second electrode is configured to deform when a predetermined force is applied thereto. The first and second jaw members including the electrodes are approximated toward one another for contact therebetween. And, one or more indentations are formed on the second electrode. The indentation(s) may be configured to provide a jaw gap that ranges from about 0.01 inches to about 0.06 inches. Moreover, during in-situ use of the pre-assembled jaw members, engagement between the at least one stop member and the at least one indentation is configured to prevent jaw splay.

Approximating the first and second jaw members including the electrodes may include compressing the first and second jaw members with a force that is at least twice as much as a force that is utilized to electrosurgically treat tissue in situ. Positioning the stop member(s) may include providing a stop member that is a ceramic dot.

A shim may be provided between the first and second opposing electrodes prior to approximating the first and second jaw members including the electrodes toward one another so as to control a depth of the at least one indentation. A portion of a bottom surface of the second electrode may be removed to facilitate forming the at least one indentation. The portion of the bottom surface may be located directly beneath the position of where the at least one indentation is to be formed. An etching process may be utilized to remove the portion of a bottom surface of the second electrode. Alternatively, a portion of a bottom surface of the second electrode may be chemically treated to facilitate forming the at least one indentation. The portion of the bottom surface may be located directly beneath the position of where the at least one indentation is to be formed.

An aspect of the present disclosure provides a method for manufacturing an electrode configuration for an electrosurgical instrument. A pre-assembled jaw configuration including first and second jaw members including respective first and second electrodes is provided. One or more stop members are positioned on the first electrode. A portion of a bottom surface of the second electrode is configured to deform when a predetermined force is applied thereto. A shim may be provided between the first and second opposing electrodes. The first and second jaw members including the electrodes are approximated toward one another for contact therebetween. And, one or more indentations are formed on the second electrode. The indentation(s) may be configured to provide a jaw gap that ranges from about 0.01 inches to about 0.06 inches. The shim may be provided between the first and second opposing electrodes prior to approximating the first and second jaw members including the electrodes toward one another so as to control a depth of the at least one indentation.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
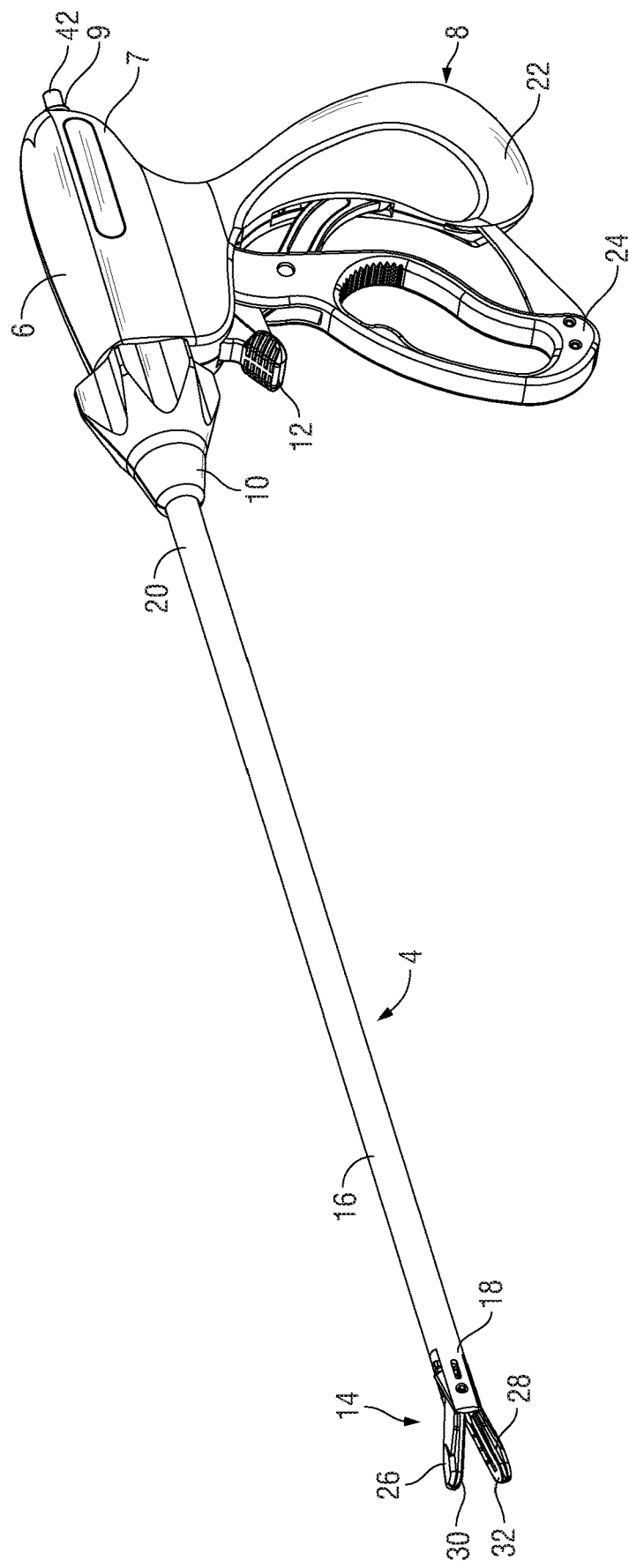
FIG. 1 is a perspective view of an electrosurgical instrument configured for use with an end effector including jaw members having electrodes manufactured in accordance with an embodiment of the instant disclosure.

FIG. 1 shows an electrosurgical forceps 4 configured for use with jaw members 26, 28 including electrodes 30, 32 formed via a method of manufacture according to an embodiment of the instant disclosure. Briefly, forceps 4 generally includes a housing 6, a shaft 16, a handle assembly 8, a rotating assembly 10 and a trigger assembly 12, which mutually cooperate with an end effector assembly 14 to grasp and treat tissue. Shaft 16 includes a distal end 18 that mechanically engages end effector assembly 14 and a proximal end 20 that mechanically engages housing 6 proximate the rotating assembly 10. Handle assembly 8 includes a fixed handle 22 and a movable handle 24. End effector assembly 14 includes jaw members 26, 28 that are movable from a first position wherein the jaw members 26, 28 are spaced relative to one another to a closed position wherein the jaw members 26 and 28 cooperate to grasp tissue therebetween. Each of the jaw members 26, 28 includes an electrically conductive tissue treatment surface 30, 32, e.g., electrodes 30, 32, that is connected to an energy source (e.g., a generator not explicitly shown) that communicates electrosurgical energy, e.g., RF energy, through tissue held between jaw members 26, 28.

With reference to FIGS. 2A-4, a method 100 utilized to manufacture jaw members 26, 28 is illustrated. In accordance with the instant disclosure, jaw members 26, 28 may, initially, be provided in a pre-assembled configuration (see FIG. 4 at step 102). Specifically, jaw members 26, 28 are manufactured with jaw housings 26a, 28a, respectively, that have been formed via one or more suitable manufacturing methods. In the illustrated embodiment, for example, jaw housings 26a, 28a are formed with respective electrodes 30, 32 coupled thereto via an overmolding process to form jaw members 26, 28.

Figure 2A:
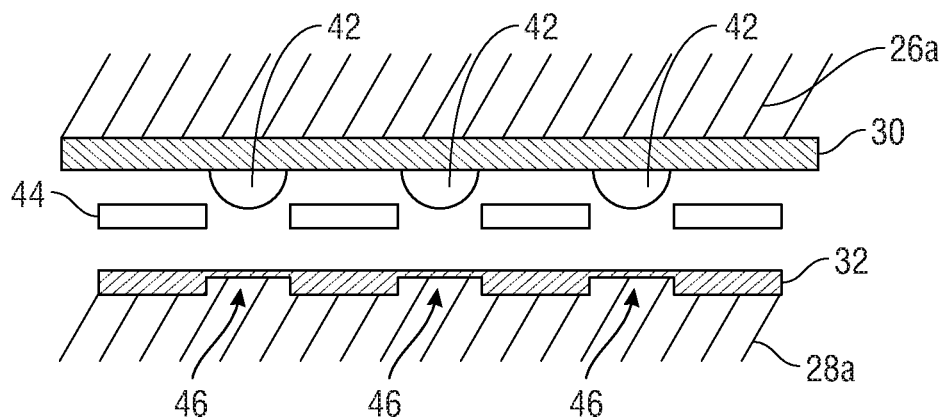
FIG. 2A is a schematic, side view of a pair of pre-assembled jaw members positioned in a pre-approximated configuration during a manufacturing process.
Figure 2B:
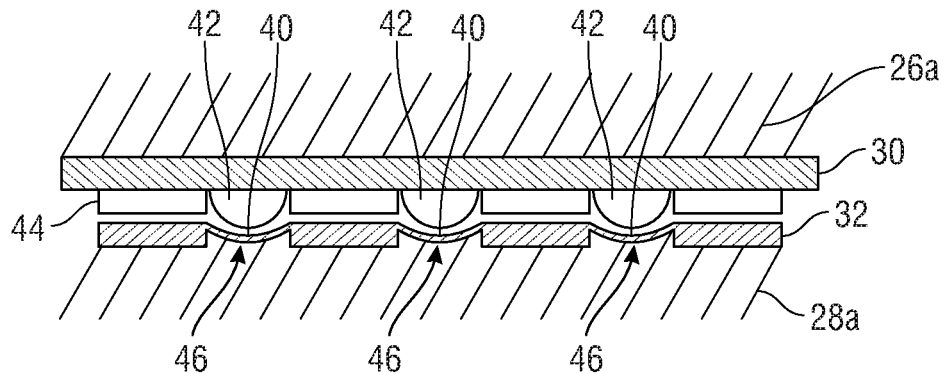
FIG. 2B is a schematic, side view of the pair of pre-assembled jaw members positioned in an approximated configuration during a manufacturing process.
Figure 3:
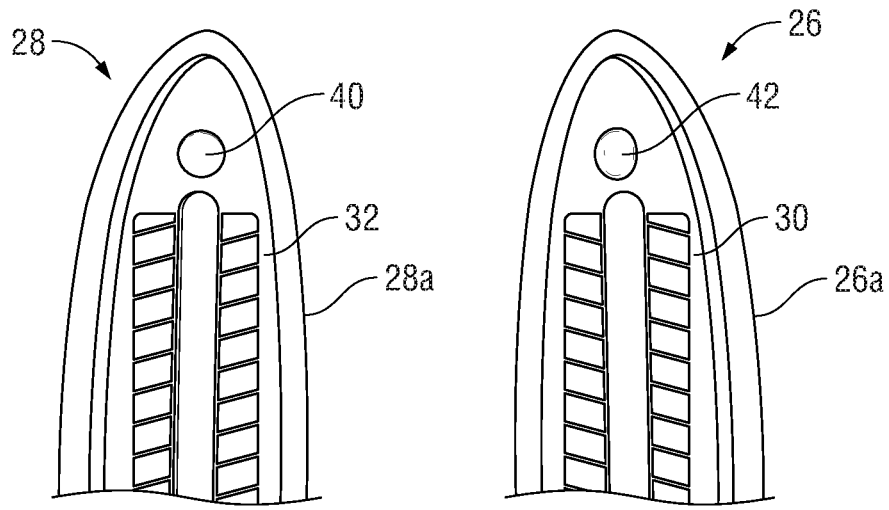
FIG. 3 is a top, plan view of the pre-assembled jaw members subsequent to formation of an indent on an electrode of one of the jaw members.
Figure 4:
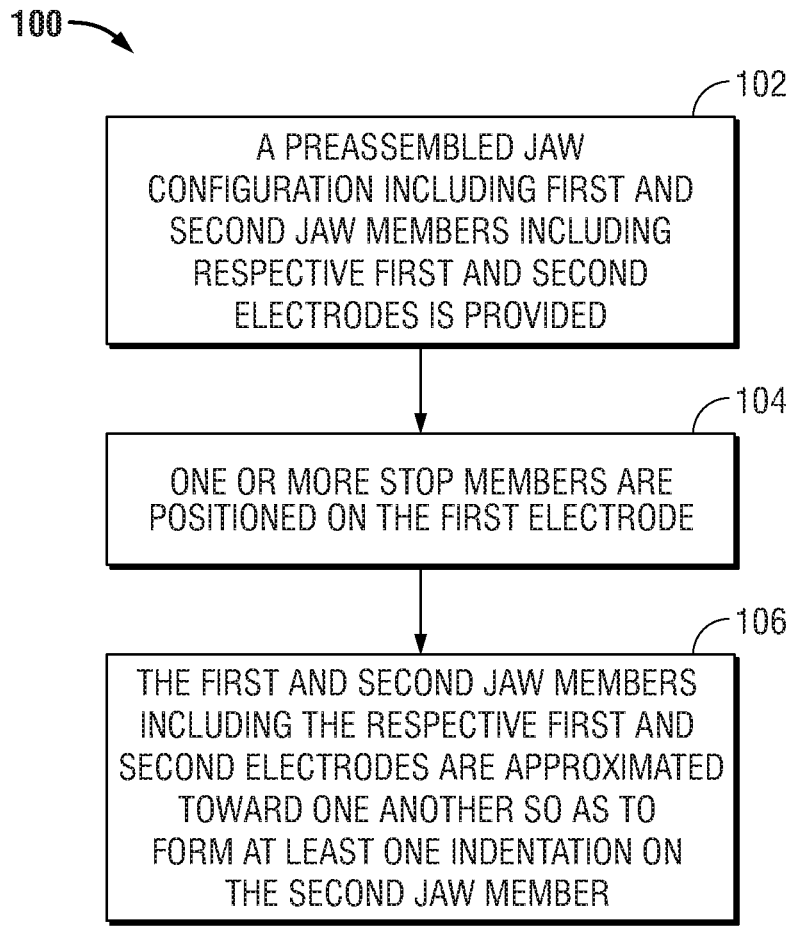
FIG. 4 is a flow-chart illustrating a method for manufacturing the jaw members.

In accordance with the instant disclosure, one or both of electrodes 30, 32 may be formed with an indention 40 and/or a stop member 42 (see FIGS. 2A-3 for example). For illustrative purposes, electrode 30 is formed with stop members 42 (see FIG. 4 at step 104) and electrode 32 is formed with indentations 40.

Stop members 42 may be formed or coupled to electrode 30 via any suitable forming or coupling methods. For example, in the illustrated embodiment stop members 42 are in the form of ceramic dots that have been affixed to a tissue contacting surface of electrode 30 via one or more suitable adhesives. Stop members 42 are configured to contact electrode 32 so as to provide a specific gap distance between jaw members 26, 28 when the jaw members 26, 28 are in a clamping configuration, see FIG. 2B for example. In accordance with the instant disclosure, a suitable gap distance between jaw members 26, 28 may range from about 0.01 inches to about 0.06 inches. In certain embodiments, the gap distance may be about 0.03 inches.

Additionally, stop members 42 are configured to contact a tissue contacting surface of electrode 32 so as to form a corresponding indentation 40 thereon. Specifically, during a manufacturing process of jaw members 26, 28, jaw members 26, 28 are approximated toward one another and compressed under a suitable compressive force so that stop members 42 contact the tissue contacting surface of electrode 32 and form a corresponding indentation thereon (see FIG. 4 at step 106), i.e., jaw members 26, 28 "over pressurized" to form the indentation. In accordance with the instant disclosure, it has been found that a suitable compressive force to indent the opposing electrode 32 when no tissue is present would be about 6 kg/cm$^3$ to about 32 kg/cm$^3$ or about twice the normal compressive force that would be utilized to seal tissue.

In embodiments, one or more shims 44 formed from any suitable material, e.g., ceramic, may be placed between electrodes 30, 32 prior to approximating the jaw members 26, 28 including electrodes 30, 32 toward one another so as to control a depth of indentation 40. Shim(s) 44 include a height that is approximately equal to a desired gap distance. In the illustrated embodiment for example, shim(s) 44 include a height that ranges from about 0.01 inches to about 0.06 inches. In certain embodiments, the height of shim(s) 44 may be about 0.03 inches.

In embodiments, prior to the overmolding process, electrodes 30, 32 may be chemically or otherwise treated. Specifically, a portion 46 of a bottom surface electrode 32 may be removed to facilitate forming indentations 40 on electrode 32. For example, in one particular embodiment, an etching process may be utilized to remove portion 46 of a bottom surface of one of the jaw members, e.g., jaw member 28. Alternatively, a portion 46 of the bottom surface of electrode 32 may be chemically treated with one or more suitable chemicals, e.g., acid, to remove portion 46 from electrode 32. In either embodiment, portion 46 is located directly beneath a position of where indentation 40 is to be formed on electrode 32, see FIGS. 2A-2B.

Method 100 may be carried out in the following manner. A pre-assembled jaw configuration including jaw members 26, 28 including respective electrodes 30, 32 thereon may be provided (see FIG. 4 at step 102). Stop member(s) 42 may be positioned on electrode 30 via one or more of the aforementioned affixation methods (see FIG. 4 at step 104). In embodiments, shim(s) 44 may also be positioned between electrodes 30, 32 prior to approximating jaw members 26, 28 including electrodes 30, 32 towards one another. Jaw members 26, 28 including electrodes 30, 32 are approximated toward one another so as to form corresponding indentation(s) 40 on electrode 32.

As noted above, during in-situ use of jaw members 26, 28, indentation(s) 40 may be configured to provide gap distance that ranges from about 0.01 inches to about 0.06 inches when jaw members 26, 28 are in a clamping configuration. Specifically, when tissue is to be sealed, stop member(s) 42 engage indentation(s) 40 to provide a specific gap distance between electrodes 30, 32. Moreover, a ratchet mechanism or other suitable device (not explicitly shown) may be provided on forceps 4 and may be configured to maintain a specific compressive force on tissue when tissue is clamped between jaw members 26, 28. The compressive force applied to tissue may range from about 3 $kg/cm^3$ to about 16 $kg/cm^3$ or about half of the compressive force that is utilized to form indentation(s) 40 on electrode 32. Further, one or more controllers or control algorithms (not explicitly shown) may be operably coupled to the forceps 4 (or provided in the generator) to control the amount of electrosurgical energy that is provided to electrodes 30, 32. All of these three factors may contribute in providing an effective, uniform and consistent tissue seal.

In accordance with the instant disclosure, the unique method 100 of manufacture of electrodes 40, 42 eliminates the aforementioned variations by incorporating self-setting features therein to precisely set a given jaw gap between the jaw members 26, 28.

Moreover, during in-situ use of jaw members 26, 28, engagement between stop member(s) 42 and indentation(s) 40 is configured to prevent jaw splay of jaw members 26, 28.

From the foregoing and with reference to the various figure drawings, those skilled in the art will appreciate that certain modifications can also be made to the present disclosure without departing from the scope of the same. For example, while the aforementioned electrodes 30, 32 have been formed via method 100 and configured for use with an endoscopic electrosurgical instrument 4, electrodes 30, 32 may be formed via method 100 and configured for use with an open type electrosurgical forceps, e.g., scissor type forceps.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for manufacturing an electrode configuration for an electrosurgical instrument, comprising:
   positioning a stop member on a first electrode of a first jaw member;
   approximating the first jaw member and a second jaw member, the approximating comprising moving one or both jaw members toward one another, wherein a portion of a bottom surface on a first side of a second electrode of the second jaw member is configured to deform when a predetermined force is applied thereto;
   removing the portion of the bottom surface of the second electrode to form a cavity therein, thereby forming a reduced thickness portion at the cavity of the second electrode as compared with the electrode thickness prior to the removing step; and
   contacting the stop member of the first electrode with a portion of a tissue-contacting surface located on a second side of the second electrode, opposite the first side of the second electrode, to deform the portion of the tissue-contacting surface into the cavity in the bottom surface of the second electrode, thereby forming a permanent indentation in the second electrode.

2. The method according to claim 1, wherein approximating the first and second jaw members includes compressing the first and second jaw members with an indentation force ranging from 6 kg/cm2 to 32 kg/cm2.

3. The method according to claim 1, wherein the stop member is a ceramic dot that gives the indentation a rounded configuration.

4. The method according to claim 1, further comprising positioning a shim between the first and second electrodes to control a depth of the indentation.

5. The method according to claim 4, wherein the shim is positioned between the first and second electrodes prior to approximating the first and second jaw members.

6. The method according to claim 1, wherein the cavity in the bottom surface of the second electrode and the indentation formed in the tissue-contacting surface of the second electrode overlap one another.

7. The method according to claim 1, wherein the portion of the bottom surface of the second electrode is removed via at least one of etching or chemical treatment.

8. The method according to claim 1, wherein the indentation is configured to provide a gap distance between the first and second jaw members that ranges from about 0.001 inches to about 0.006 inches.

9. The method according to claim 1, wherein the reduced thickness portion of the second electrode is further defined between the tissue-contacting surface and the bottom surface of the second electrode, and wherein deforming the portion of the tissue-contacting surface includes bending the reduced thickness portion about opposite ends thereof to move a middle section of the reduced thickness portion deeper into the cavity than the opposite ends of the reduced thickness portion.

* * * * *